United States Patent [19]

Elmendorp

[11] 4,197,261

[45] Apr. 8, 1980

[54] PROCESS FOR THE PURIFICATION OF BENZALDEHYDE

[75] Inventor: Jan Elmendorp, Brunssum, Netherlands

[73] Assignee: Stamicarbon, B.V., Geleen, Netherlands

[21] Appl. No.: 952,609

[22] Filed: Oct. 18, 1978

[30] Foreign Application Priority Data

Oct. 18, 1977 [NL] Netherlands ............................ 7711393

[51] Int. Cl.$^2$ ............................................. C07C 45/24
[52] U.S. Cl. ........................................................ 260/599
[58] Field of Search .......................................... 260/599

[56] References Cited

U.S. PATENT DOCUMENTS

| | | | |
|---|---|---|---|
| 1,636,854 | 7/1927 | Craver | 260/599 |
| 2,199,585 | 5/1940 | Bone et al. | 260/599 |
| 3,423,466 | 1/1969 | Guyer, Jr. et al. | 260/599 |

OTHER PUBLICATIONS

Tobolsky et al., Organic Peroxides (1954) p. 37.
Crenne, Chemical Abstracts, vol. 78 (1973) 62040g.
Crenne, Riv. Ital. Essenze, Profumi, Piante Off., Aromi, Saponi, Cosmet., Aerosol (1972) vol. 57(7) pp. 487-492.

*Primary Examiner*—Bernard Helfin
*Attorney, Agent, or Firm*—Cushman, Darby & Cushman

[57] ABSTRACT

Crude benzaldehyde, and especially benzaldehyde prepared by the oxidation of toluene with a gas containing molecular oxygen, will contain certain impurities which will cause unwarranted discoloration and olfactory problems. These impurities can be effectively removed by treating the benzaldehyde with an oxidizing agent and then distillation.

23 Claims, No Drawings

PROCESS FOR THE PURIFICATION OF BENZALDEHYDE

The present invention is a new and novel process for the purification of benzaldehyde and, is in particular, a significant improvement in the purification of benzaldehyde prepared by the oxidation of toluene with a gas containing molecular oxygen.

BACKGROUND OF THE INVENTION

Benzaldehyde is an important starting material in various chemical synthesis, including those relating to the synthesis of scents and flavors. In these applications the benzaldehyde is often required to have a high degree of purity, but unfortunately crude benzaldehyde, and especially benzaldehyde prepared by the oxidation of toluene with a gas containing molecular oxygen, will contain certain impurities that are very difficult to remove. One very significant problem presented by these impurities is that it is particularly difficult to obtain a product from such crude benzaldehyde that will satisfy the requirements of olfactory specifications. Furthermore, the presence of such impurities also causes a quite rapid discoloration of the benzaldehyde upon storage. Such discoloration will occur even at very low concentrations of the impurities, such as a few p.p.m. by weight.

One suggested solution which appears in Japanese Patent Publication 24.467/74 is to purify crude benzaldehyde by treating it with an aqueous solution of sodium hydroxide. However, this method of purification does not give satisfactory results. Benzaldehyde treated in this manner is still found to discolor quite rapidly.

OBJECT OF THE INVENTION

The present invention provides a solution to this problem. According to the present invention, pure benzaldehyde is prepared by treating impure benzaldehyde with an oxidizing agent and distilling it.

It is particularly surprising that crude benzaldehyde can be purified in this manner. This is because, that while it is commonly known that oxidizing agents can readily oxidize benzaldehyde, colored reaction products may be concurrently formed. See, e.g., Beilsteins Handbuch der Organischen Chemie, 4 Auflage, 7, 179-180 and 7-III, 811. Another advantage of the process of the present invention is that the loss of benzaldehyde is very small, for example, in the order of about 0.5 to about 1% by weight. Importantly, benzaldehyde which meets the demands of olfactory specifications can be obtained, even from crude benzaldehyde prepared by the oxidation of toluene.

DESCRIPTION OF THE INVENTION

In accordance with the process of the present invention, impure benzaldehyde is treated with an oxidizing agent and then distilled. If so desired, the treatment with the oxidizing agent and the distillation may be carried out simultoneously.

Suitable oxidizing agents which can be used in the process according to the present invention are, for example, gases containing molecular oxygen, such as air, pure oxygen and nitrogen-oxygen mixtures with a different composition from air. Peroxide agents are also extremely suitable. Other oxidizing agents, such as, potassium permanganate or potassium (di)chromate, are slightly less suitable. The oxidizing agents are used by preference in amounts between about 1 and about 5000 mgramatoms, calculated as active oxygen, per kg benzaldehyde.

The amounts of the gas containing molecular oxygen should range between about 0.1 and about 5 liters (N.T.P.) and preferably range between about 0.5 and about 2 liters (N.T.P.), calculated as molecular oxygen, per hour and per kg of benzaldehyde. Larger amounts may be used, but offer no significant advantage. The time of treatment may range, for instance, between about 0.5 and about 10 hours.

The peroxide agent used by preference is hydrogen peroxide, e.g., as a 30% by weight aqueous solution which is a normal commercial product. If desired, a more dilute aqueous solution may also be used, such as from about 2% to about 30% by weight solution. Also more concentrated aqueous solutions of up to even about 90% or higher by weight may be used, but feed control will be more difficult. The amount of hydrogen peroxide, calculated as $H_2O_2$, relative to the benzaldehyde preferably ranges between about 3 and about 1500 mmoles per kg, which are, respectively, about 0.01 to about 5% by weight of hydrogen peroxide. Larger amounts of hydrogen peroxide may be used, but will only increase the treating cost. Preferably, an amount of hydrogen peroxide of about 3 to about 150 mmoles per kg of benzaldehyde is used.

Examples of other suitable peroxide agents are percaboxylic acids and their salts, e.g., perbenzoic acid or peracetic acid; and inorganic persalts, e.g., potassium persulphate. The amounts of these to be used, calculated as moles of peroxide per kg of benzaldehyde, correspond to those of hydrogen peroxide.

The treatment of the crude benzaldehyde with an oxidizing agent may be effected in the liquid phase at temperatures of, e.g., from about 20° to about 200° C. If a peroxide agent is used as the oxidizing agent, temperatures ranging from approximately room temperature to elevated temperature can be used. If a gas containing molecular oxygen is used as the oxidizing agent, the use of elevated temperature, preferably between about 75° and about 175° C. is desirable. Temperatures higher than about 200° C. may be used, but will result in undesirably great losses of benzaldehyde. Further, such temperatures are less desirable for reasons of safety.

The reaction pressure is less critical and may range, for instance, between about 10 and about 1000 kPa. A pressure approximately equal to atmospheric pressure for example, of between about 50 and about 200 kPa, is to be preferred for practical considerations.

The benzaldehyde treated with the oxidizing agent is then distilled. If so desired, the treatment with an oxidizing agent and the distillation may be effected simultaneously. The distillation may be effected at atmospheric or elevated pressure, but, preferably, is carried out at reduced pressure, e.g., a pressure of about 2 to about 35 kPa.

It is extremely important to note that if hydrogen peroxide is used as the oxidizing agent, an important advantage of the process of the present invention will surface. This is because the only by-product with a low boiling point is water which is usually also present in the hydrogen peroxide as the diluting agent. The water can be separated out during the distillation in a simple way as the water-benzaldehyde azeotrope which has a lower boiling point than benzaldehyde.

It may also be advantageous to decompose any unconverted peroxide agent before the distillation. This can be done thermally, for example, by heating the benzaldehyde containing the peroxide agent to a temperature of, e.g., about 100° C. to about 200° C., preferably from about 120° to about 160° C. If desired, a catalyst for the decomposition of peroxides such as a heavy-metal salt, for instance a cobalt salt of an iron salt may be added in this step. Amounts of heavy metal of about 0.1 to about 20, and preferably of about 0.5 to about 2 p.p.m. by weight relative to the benzaldehyde are sufficient for a satisfactory catalytic action. Larger amounts may be used, if so desired.

EXAMPLES

The invention will be elucidated with reference to the following non-restricting examples and comparative experiments. The color values in degrees Hazen (°H) were determined by ASTM D1209/62.

EXAMPLE I

A sample of crude benzaldehyde prepared by the oxidation of toluene in the liquid phase by means of a gas containing molecular oxygen with the use of a homogeneous cobalt catalyst was distilled in a sievetray column with 30 trays at a top pressure of 20 kPa and with a reflux ratio of 1:3. During the distillation 5 liters (N.T.P.) of air per liter of liquid benzaldehyde were passed through per hour. The color value of the main fraction was lower than the detection limit of 5° H. After 20 days storage in a dark-brown bottle under a nitrogen atmosphere, the color value was found still to be no more than 5° H. The color value of the crude benzaldehyde used as the starting product was much higher than the limit of determination of 30° H.

EXAMPLE II

A sample of the same liquid crude benzaldehyde as used in Example I was treated for 1 hour at 140° C. with a 0.5%-by weight hydrogen peroxide in the form of a 30%-by weight aqueous solution. Next, 5 p.p.m. by weight of cobalt (as acetate) were added and the mixture was distilled under the same conditions as in Example I, but without air being passed through. The color value of the main fraction was below the 5° H limit and was 5° H upon 20 days storage in the way described in Example I.

EXAMPLE III

A sample of the same liquid crude benzaldehyde as used in Example I was heated at 160° C. for 2 hours while 10 liters (N.T.P.) of air per liter of benzaldehyde were passed through per hour. The mixture was then distilled in a sieve-tray column with 30 trays at a top pressure of 13 kPa and with a reflux ratio of 1:3 without air being passed through. The color value of the main fraction was below the 5° H limit. The color value was still below this limit upon 14 days storage in the way described in Example I.

EXAMPLE IV

A sample of the same liquid crude benzaldehyde as used in Example I was treated at 140° C. for 1 hour with 2%-by weight perbenzoic acid. Next, 5 p.p.m. by weight of cobalt (as acetate) were added and the mixture was distilled under the same conditions as in Example II. The color value of the main fraction was below the 5° H limit, even upon 14 days storage in the way described in Example I.

Comparative Example A

A sample of the same liquid crude benzaldehyde as used in Example I was distilled without the use of an oxidizing agent, but under otherwise similar conditions. The color value of the main fraction was 25° H and had risen to far over the limit of the determination (30° H) after 10 days storage in the way described in Example I.

Comparative Example B

A sample of the same crude benzaldehyde as used in Example I was stirred at 25° C. for 30 minutes with half the weight of 2.5%-by weight aqueous sodium-hydroxide solution. The benzaldehyde layer was separated and distilled. The color value of the main fraction was far over 30° H.

What is claimed is:

1. Process for the purification of benzaldehyde comprising the steps of,
    (a) treating impure benzaldehyde with an amount of about 1 to about 5000 mgramatoms of an oxidizing agent, calculated as active oxygen per kg of benzaldehyde at a temperature from about 20° C., to about 200° C., and
    (b) distilling said treated benzaldehyde.
2. The process of claim 1, wherein the treatment with an oxidizing agent and the distillation are carried out simultaneously.
3. The process of either claim 1 or 2, wherein the oxidizing agent is a peroxide.
4. The process of claim 3, wherein the peroxide is hydrogen peroxide.
5. The process of claim 3, wherein the amount of peroxide used is from about 3 mmoles to about 1500 mmoles of peroxide per kg of benzaldehyde.
6. The process of claim 5, wherein the amount of peroxide used is from about 3 mmoles to about 150 mmoles of peroxide per kg of benzaldehyde.
7. Process of either claim 1 or 2, wherein the oxidizing agent is a gas containing molecular oxygen.
8. Process of claim 7, wherein the oxidizing agent is air.
9. Process of claim 7, wherein from about 0.1 to about 5 liters (N.T.P.), calculated as molecular oxygen per kg of benzaldehyde and per hour, are passed through the benzaldehyde for a period of about 0.5 to about 10 hours.
10. Process of claim 9, wherein from about 0.5 to about 2 liters (N.T.P.), calculated as molecular oxygen per kg of benzaldehyde and per hour, are passed through the benzaldehyde.
11. Process of claims 1 or 2, wherein the oxidizing agent is a gas containing molecular oxygen and the treatment with said agent is carried out at a temperature of from about 75° C. to about 175° C.
12. Process of either claim 1 or 2, wherein the benzaldehyde being purified had been prepared by the oxidation of toluene with a gas containing molecular oxygen and the oxidizing agent is also a gas containing molecular oxygen.
13. Process of claim 12, wherein the oxidizing agent used to treat the benzaldehyde is air.
14. Process of claim 12, wherein from about 0.1 to about 5 liters (N.T.P.), calculated as molecular oxygen per kg of benzaldehyde and per hour, are passed through the benzaldehyde for a period of about 0.5 to about 10 hours.

15. Process of claim 14, wherein from about 0.5 to about 2 liters (N.T.P.), calculated as molecular oxygen per kg of benzaldehyde and per hour, are passed through the benzaldehyde.

16. Process of claim 15, wherein the treatment with air is carried out at a temperature of from about 75° C. to about 175° C.

17. Process for the purification of benzaldehyde comprising the steps of,
(a) treating impure benzaldehyde with an amount of about 1 to about 5000 mgramatoms of peroxide agent calculated as active oxygen per kg of benzaldehyde at a temperature from about 20° C. to about 200° C.,
(b) decomposing unconverted peroxide agent, and
(c) distilling said treated benzaldehyde.

18. Process of either claims 1, 2 or 17, wherein the benzaldehyde being purified had been prepared by the oxidation of toluene with a gas containing molecular oxygen.

19. Process of claim 18, wherein the oxidizing agent is a peroxide.

20. Process of claim 19, wherein the peroxide is hydrogen peroxide.

21. Process of claim 19, wherein the amount of peroxide used is from about 3 mmoles to about 1500 mmoles of peroxide per kg of benzaldehyde.

22. Process of claim 21, wherein the amount of peroxide used is from about 3 mmoles to about 150 mmoles of peroxide per kg of benzaldehyde.

23. Process of claim 18, wherein the treatment with the oxidizing agent is carried out at a temperature of from about 20° C. to about 200° C.

* * * * *